United States Patent [19]
Gillespie

[11] Patent Number: 5,342,199
[45] Date of Patent: Aug. 30, 1994

[54] CYLINDRICAL DENTAL IMPLANT

[75] Inventor: Edward S. Gillespie, Ardmore, Okla.

[73] Assignee: Imtec Corporation, Ardmore, Okla.

[21] Appl. No.: 134,344

[22] Filed: Oct. 8, 1993

[51] Int. Cl.$^5$ .............................................. A61C 8/00
[52] U.S. Cl. ...................................................... 433/173
[58] Field of Search ............... 433/173, 174, 175, 176, 433/201.1; 623/16

[56] References Cited

U.S. PATENT DOCUMENTS

| | | | |
|---|---|---|---|
| 1,479,508 | 1/1924 | Maeulen et al. | 433/221 |
| 2,721,387 | 10/1955 | Ashuckian | 433/173 |
| 3,064,645 | 11/1962 | Ficat et al. | 433/173 |
| 3,579,831 | 5/1971 | Stevens et al. | 433/201.1 |
| 3,707,006 | 12/1972 | Bokoros et al. | 3/1 |
| 3,797,113 | 3/1974 | Brainin | 433/201.1 |
| 4,382,791 | 5/1983 | Misch | 433/172 |
| 4,447,209 | 5/1984 | Sutter | 433/173 |
| 4,622,010 | 11/1986 | Koch | 433/173 |
| 4,624,673 | 11/1986 | Meyer | 623/16 |
| 4,722,688 | 2/1988 | Lonca | 433/173 |
| 4,854,873 | 8/1989 | Linden | 433/173 |
| 4,904,187 | 2/1990 | Zingheim | 433/173 |
| 4,915,628 | 4/1990 | Linkow et al. | 433/173 |
| 5,006,070 | 4/1991 | Komatsu | 433/173 |
| 5,049,073 | 9/1991 | Lauks | 433/173 |
| 5,076,788 | 12/1991 | Niznick | 433/173 |

OTHER PUBLICATIONS

C. English, "An Overview of Implant Hardware", JADA, vol. 121, Sep. 1990, 7 pages.
"Hexed-Head® Implant System", Spring 1993 Catalog, Imtec Corporation, 12 pages.

*Primary Examiner*—John J. Wilson
*Attorney, Agent, or Firm*—Dunlap, Codding & Lee

[57] ABSTRACT

An improved cylindrical dental implant for anchoring a dental prosthesis in a hole formed in a jawbone comprising an elongated cylindrical member having a first end adapted to be inserted into the hole and a second end adapted to receive the dental prosthesis. At least one wedge member radially extends from the cylindrical member to effect immediate fixation of the cylindrical member in the hole. The wedge member has a base portion connected to the outer peripheral surface of the cylindrical member and a tapered portion having a first planar face and a second planar face. The first planar face and the second planar face intersect to form a thin longitudinally extending edge.

9 Claims, 2 Drawing Sheets

CYLINDRICAL DENTAL IMPLANT

BACKGROUND OF THE INVENTION

1 Field of the Invention

The present invention relates generally to dental implants, and more particularly, but not by way of limitation, to an improved cylindrical dental implant capable of being immediately fixed in a hole formed in bone.

2 Description of Related Art

The use of cylindrical dental implants to anchor dental prostheses in bone is well known. Generally, a hole is drilled in the jawbone of a person and an implant is driven into the hole. After bone has been allowed to heal and regenerate about the implant, the prosthesis is secured to the implant.

To function effectively, it is important that the implant remain securely fixed in the bone. The ability of the implant to remain fixed to the bone is dependent upon the ability of the implant to react as part of the bone, or more specifically, the ability of the bone to adaptively seal about the implant. Because of the rotational and lateral forces that are exerted on implants by activities such as chewing food, the sealing of the bone about the implant alone is often not sufficient to keep the implant permanently fixed in the hole. To this end, various attempts have been made to mechanically enhance the interaction between the bone and the implant.

Several prior art implants have been proposed which employ grooves or flutes along the periphery of the implants. The grooves and flutes are intended to receive new bone growth and thus inhibit rotation and vertical displacement of the implant relative to the bone. While these devices have achieved varying degrees of success, problems have nevertheless been encountered. For example, when drilling the hole in which the implant is disposed, it is often difficult to form a perfectly round hole because of the limited space and the angle from which one must drill, especially when drilling a hole in the back of a patient's mouth. The holes will often end up oval-shaped or significantly oversized. Since cylindrical implants are designed to be press fitted in the hole, a hole that is not precisely dimensioned will not adequately hold the implant during the important initial stages of the healing period. As such, the chances that the implant can be upset during the healing period are increased.

In an attempt to ensure that the implant remains in a fixed position during the healing period, prior art implants have been proposed which employ projecting members that extend from the outer surface of the implant and cut into the bone as the implant is driven into the hole. One such implant is disclosed in U.S. Pat. No. 4,854,873, issued to Linden. The Linden patent discloses a cylindrical implant with a flat proximal end and a rounded distal end. Projecting members are formed on the cylindrical surface in such a manner that the projecting members taper from the proximal end toward the distal end. As the implant is driven into the hole, the projecting members cut a vertical channel in the bone. The implant is then twisted thereby forming undercuts in the bone which function to rigidly lock the implant in position.

U.S. Pat. No. 4,915,628, issued to Linkow et al., discloses an implant having rounded longitudinal columns projecting outwardly from the outer surface of the implant. A curved cutting edge is formed on one end of the columns. During insertion of the implant into a hole, the cutting edges cut slots in the bone. The slots receive the longitudinal columns so as to prevent the implant from rotating within the hole.

As with the implants that employ grooves and flutes, problems have been encountered with use of the prior art implants that employ outwardly extending projecting members, including those taught by the above mentioned patents. In particular, the cutting and crushing of bone, which results from the use of the prior art implants mentioned above, substantially increases the healing period. Cutting and crushing of bone further effects a great deal of trauma to the bone which in turn increases the chances that the bone will fail to hold the implant.

The round designs of dental implants have many inherent weaknesses. Their lack of resistance to rotational forces and of firm immediate fixation are noted by all. An oval or even modified figure "8" design would be better. Why then is virtually every major dental implant in current production round? The answer is that the only uniform, repeatable, predictable receptor site in the bone must be mechanically produced by dental cutting drills. This dictates that a hole must be round and of differing measured lengths, thus the implant must also be round.

While the referenced previous art has attempted to make improvements on the standard cylinder implant, the unique design of the present invention provides the maximum capacity of immediate fixation with the minimum of trauma or displacement of bone.

In view thereof, it can be seen that a need has long existed for an improved cylindrical dental implant that can be immediately fixed in bone, while not excessively traumatizing or damaging the bone. It is to such an improved dental implant that the present invention is directed.

SUMMARY OF THE INVENTION

The present invention is directed to an improved dental implant which is adapted to be immediately fixed in a hole formed in a jawbone without effecting undue trauma or damage to the bone. Broadly, the dental implant of the present invention comprises an elongated cylinder having a first end, a second end and an outer peripheral surface. The first end of the cylinder is adapted to be inserted into a hole formed in a jawbone and the second end is adapted to receive a dental prosthesis. To effect immediate fixation of the cylinder in the hole, the cylinder is provided with at least one wedge member which radially extends therefrom. The wedge member has a base portion connected to the outer peripheral surface of the cylinder and a tapered portion having a first planar face and a second planar face. The first planar face and the second planar face intersect to form a thin longitudinally extending edge which will cause the wedge member to wedge into the bone as the implant is driven into the hole.

An object of the present invention is to provide an improved cylindrical dental implant which can be immediately fixed in a hole formed in bone.

Another object of the present invention, while achieving the above stated object, is to provide an improved cylindrical dental implant which is easy to insert into position and which is fixed in the hole without effecting undue trauma to the bone.

Another object of the present invention, while achieving the above stated objects, is to provide an improved cylindrical dental implant that is durable in construction, economical to manufacture and which overcomes the disadvantages of the prior art.

Other objects, advantages and features of the present invention will be apparent from the following detailed description when read in conjunction with the drawings and the appended claims.

DETAILED DESCRIPTION

Figure 1:
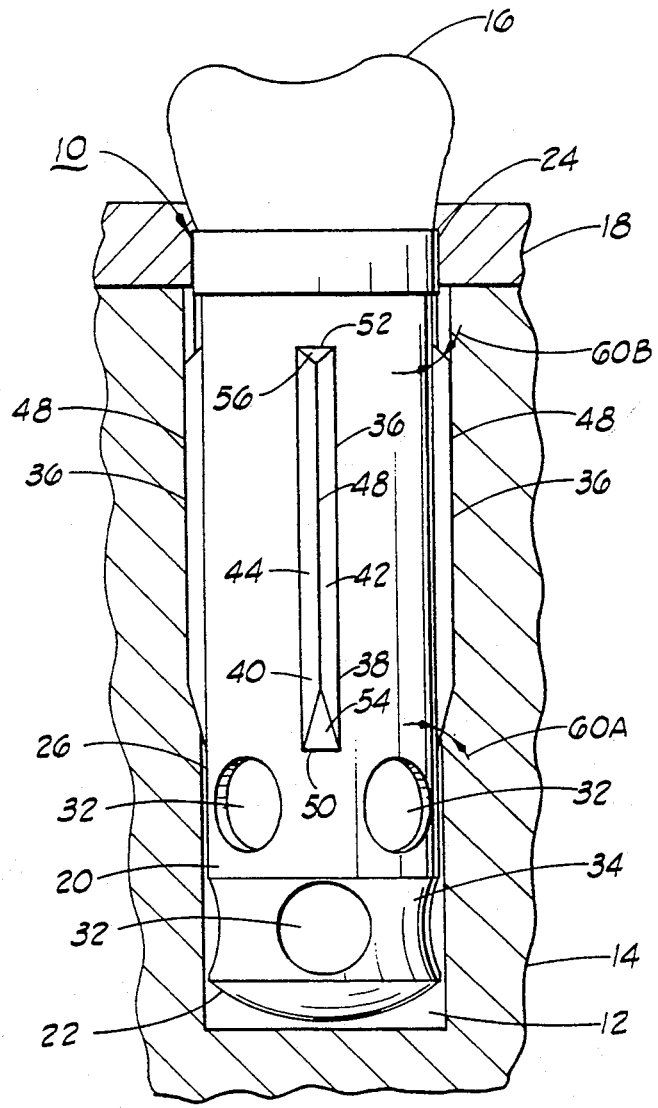
FIG. 1 is an elevational view, partially in cross section, of a dental implant constructed in accordance with the present invention disposed in a hole formed in a jawbone and having a dental prosthesis attached thereto.

Referring now to the drawings, and more particularly to FIG. 1, a dental implant 10 constructed in accordance with the present invention is shown disposed in a hole 12 formed in a jawbone 14. The dental implant 10 is shown anchoring a dental prosthesis 16 in the jawbone 14 with the prosthesis 16 extending through gum tissue 18 which covers the jawbone 14.

Figure 2:
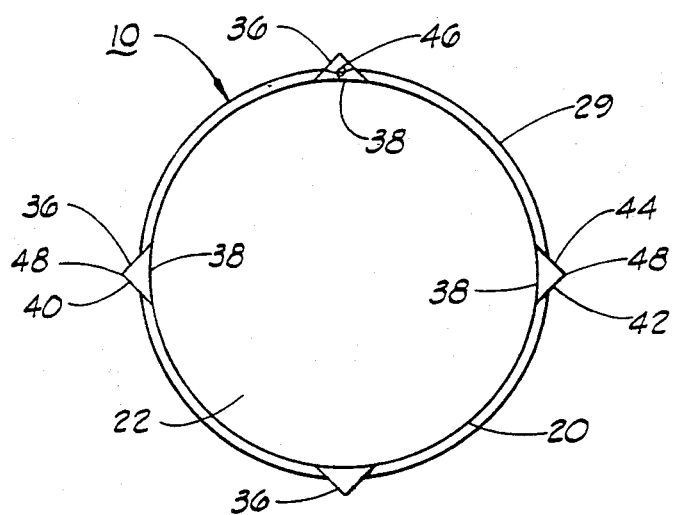
FIG. 2 is a bottom plan view of the dental implant of the present invention.
Figure 3:
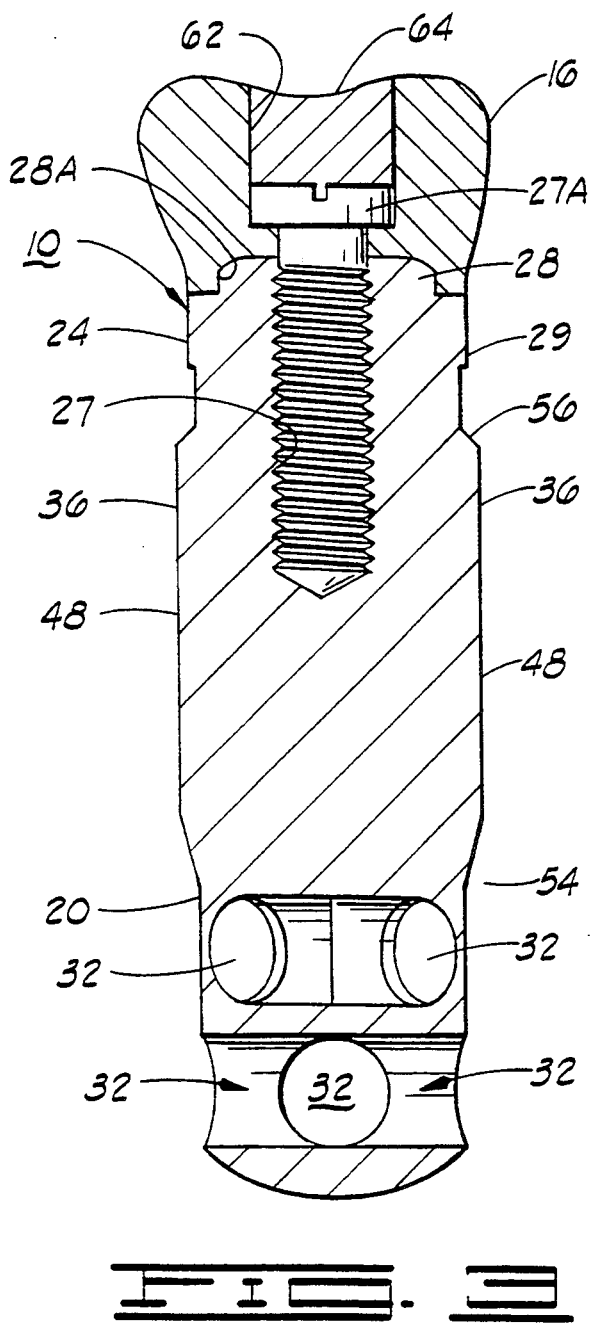
FIG. 3 is a vertical cross section of the dental implant of FIG. 1 shown removed from the jawbone.

The dental implant 10, as shown in FIGS. 1-3, includes a cylindrical member or cylinder 20 having a first end 22, a second end 24 and an outer peripheral surface 26. The cylinder 20 is preferably constructed of a titanium alloy and is dimensioned to enable the implant 10 to be fixed in the jawbone 14 so that the top of the prosthesis 16 is supported near the occlusal plane of adjacent teeth. The first end 22 of the cylinder 20 is adapted to be inserted into the hole 12. To this end, the first end 22 is preferably rounded to facilitate insertion of the cylinder into the hole 12.

As best shown in FIG. 3, the second end 24 of the cylinder 20 is adapted to receive the prosthesis 16. More specifically, the second end 24 is provided with a threaded bore 27 which extends longitudinally into the cylinder 20. The threaded bore 27 is matable with an attachment screw 27A that is insertable through the prosthesis 16 and used to secure the prosthesis 16 to the implant 10 as described below. To prevent the prothesis 16 from rotating about the implant 10, the second end 24 of the cylinder 20 is provided with an externally hexed head 28 which is dimensioned to be matably received in a hexagonal-shaped recess 28A provided in the prosthesis 16.

The second end 24 of the cylinder 20 further includes a collar 29 which is dimensioned to ensure that the implant 10 is set at the proper depth in the hole 12 and that the prosthesis 16 will be properly positioned with respect to the adjacent teeth. Because the collar 29 is in contact with the gum tissue 18, the collar 29 is provided with a polished surface which functions to inhibit bacterial growth on the collar 29.

The remainder of the cylinder 20 is coated with a biocompatible material which minimizes the possibility of infection and provides a textured surface over the cylinder 20 which enhances the ability of the bone to interact with the cylinder 20. Any suitable biocompatible material can be used, however, a titanium plasma spray or a combination of hydroxylapatite and titanium plasma spray is preferred.

To further enhance the interaction between the bone 14 and the implant 10 after the bone 14 has had an opportunity to regenerate about the implant 10, the cylinder 20 is provided with a plurality of openings 32. The openings 32 are provided to receive new bone growth which acts to inhibit rotational and vertical displacement of the implant 10 and to secure the implant 10 in the hole 12 after a sufficient healing period has passed.

FIGS. 1 and 3 illustrate the openings 32 as being formed near the first end 22 of the cylinder 20 in two rows with the openings 32 in each row traversing the cylinder 20 and being spaced apart 90 degrees. The openings 32 are further formed so that the openings 32 are spaced apart 45 degrees with respect to the adjacent openings 32 in the adjacent row. It will be appreciated by those skilled in the art that the openings 32 can be oriented in numerous ways dependant on the space limitations. For example, with a relatively small implant, such as a cylinder having a length of 8-10 mm, it is preferable that only one row of openings 32 be formed in the cylinder 20 with the openings extending only partially into the cylinder 20 to maintain the mechanical integrity of the cylinder.

As shown in FIGS. 1 and 3, the cylinder 20 is provided with an annular depression 34 to further inhibit the vertical displacement of the implant 10. The annular depression 34 is formed on the outer peripheral surface 26 of the cylinder 20 near the first end 22 thereof such that the annular depression 34 traverses the row of openings 32 nearest the first end 22 of the cylinder 20. Although not illustrated herein, it will be obvious that another annular depression that traverses the second row of openings 32 could also be formed in the cylinder 20.

To effect immediate fixation of the implant 10 in the hole 12, the implant 10 is provided with four elongated wedge members 36 (as shown in FIG. 2) on the outer peripheral surface 26 of the cylinder 20. While it is preferred that four wedge members 36 be formed on the cylinder 20 with the wedge members being equally spaced about the cylinder 20, it will be appreciated by those skilled in the art that as few as one wedge member 36 will effectively function to fix the implant 10 in the bone 14 upon insertion of the implant 10 into the hole 12.

The wedge members 36 extend radially from the outer peripheral surface 26 of the cylinder 20 and are dimensioned to extend longitudinally along the outer peripheral surface 26 from near the collar 29 to near the openings 32. Each of the wedge members 36 has a base portion 38 and a tapered portion 40. The base portion 38 is connected to the outer peripheral surface 26 of the cylinder 20 such that the tapered portion 40 extends radially form the cylinder 20.

The tapered portion 40 includes a first planar face 42 and a second planar face 44. The first planar face 42 and the second planar face 44 are formed at an angle 46 (FIG. 2) with respect to one another such that the intersection of the first planar face 42 and the second planar face 44 defines a thin longitudinally extending edge 48. The edge 48 will cause the wedge member 36 to wedge or penetrate into the bone 14 as the implant 10 is driven into the hole 12. The angle 46 is preferably about 90 degrees.

Each wedge member 36 further has a first end portion 50 and a second end portion 52 with the first end portion 50 being oppositely disposed from the second end portion 52. The first and second end portions 50 and 52 of the tapered portion 40 have a planar face 54 and 56, respectively. The planar face 54 of the first end portion 50 extends between the first and second planar faces 42, 44 of the tapered portion 40 and the base portion 38. Likewise, the planar face 56 of the second end portion 52 extends between the first and second planar faces 42, 44 of the tapered portion 40 and the base portion 38.

The planar faces 54 and 56 of the first and second end portions 50, 52 are angled toward one another at angles 60A and 60B, respectively (FIG. 3), with respect to the outer peripheral surface 26 of the cylinder 20. To facilitate insertion of the wedge members 36 into the hole 12, the angle 60A is preferably not greater than about 15 degrees. The angle 60B is preferably about 45 degrees.

When installing the implant 10 in a patient, an incision is made through the gum tissue 18 and the hole 12 is surgically drilled in the jawbone 14. The diameter of the hole 12 is preferably slightly larger than the diameter of the cylinder 20 to ensure that the wedge members 36 will be in contact with the bone 14 when the implant 10 is inserted into the hole 12. After the hole 12 has been prepared, the implant 10 is driven into the hole 12 with a mallet. As the implant 10 is driven into the hole 12, the configuration of the wedge members 36 causes the wedge members 36 to penetrate or wedge into the bone 14 thereby immediately fixing the implant 10 in the hole 12.

After the implant has been positioned in the hole, a healing screw (not shown) is inserted into the threaded bore 27 and the gum tissue 18 is sutured over the healing screw. After a predetermined healing period has passed, the healing screw is removed and the prosthesis 16 is secured to the implant 10 by first placing the prosthesis 16 on the implant 10 so that the hexagonal-shaped recess 28A of the prosthesis mates with the externally hexed head 28 of the cylinder 20. Next, the prosthesis 16 is secured to the implant 10 with the attachment screw 27A which is inserted through the prosthesis 16 through a screw receiving hole 62. After the attachment screw 27A has been secured, the screw receiving hole 62 is filled with a suitable material 64.

One of the advantages of utilizing the present invention is that the configuration of the wedge member 36 ensures a tight fit in the hole 12 for the implant 10 so long as the diameter of the hole is greater than the diameter of the cylinder and less than the diameter of the implant taken at the edges 48. To this end, it will be appreciated by those skilled in the art that the tolerances between the hole 12 and the implant 10 do not have to be extremely close. That is, the diameter of the hole 12 can vary between the edge 48 and the base portion 38 of the wedge member 36 and still tightly support the implant 10. The configuration of the wedge members 36 further provide that the bone 14 will not be subjected to any undue trauma as the implant is inserted into the hole, therefore, making it is less likely that the bone will fail when force is exerted on the implant.

From the above description it is clear that the present invention is well adapted to carry out the objects and to attain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and as defined in the appended claims.

What is claimed is:

1. A dental implant for anchoring a dental prosthesis in a hole formed in a jawbone, comprising:

a cylindrical member having a first end, a second end and an outer peripheral surface, the first end being adapted to be inserted into the hole and the second end being adapted to receive the prosthesis; and at least one wedge member radially extending from the cylindrical member and having a base portion connected to the outer peripheral surface of the cylindrical member and a tapered portion having a first planar face and a second planar face, the first planar face and the second planar face being angled toward one another such that the intersection of the first planar face and the second planar face defines a thin longitudinally extending edge, the wedge member further comprising a first end portion angled to facilitate insertion of the wedge member into the hole, the first end portion comprising a planar face extending between the first and second planar faces of the tapered portion and the base portion.

2. The dental implant of claim 1 wherein the wedge member further comprises a second end portion oppositely disposed from the first end portion, the second end portion comprising a planar face extending between the first and second planar faces of the tapered portion and the base portion.

3. The dental implant of claim 2 wherein the angle between the planar face of the first end portion and the base portion is about 15 degrees.

4. The dental implant of claim 2 wherein the second end of the cylindrical member has a threaded bore extending longitudinally therethrough and wherein the prosthesis is secured to the second end of the cylindrical member with an attachment screw threadably engagable with the threaded bore.

5. The dental implant of claim 4 wherein the second end of the cylindrical member has an externally hexed head matable with a portion of the prosthesis.

6. The dental implant of claim 5 wherein the first end of the cylindrical member is rounded.

7. The dental implant of claim 6 wherein the second end of the cylindrical member has a polished surface and wherein the remainder of the cylindrical member is coated with a biocompatible material which forms a textured surface.

8. The dental implant of claim 7 wherein the cylindrical member further comprises a plurality of openings formed in the outer peripheral surface of the cylindrical member near the first end thereof.

9. The dental implant of claim 8 wherein the cylindrical member further comprises an annular depression formed near the first end of the cylindrical member to inhibit vertical displacement of the cylindrical member in the hole.

* * * * *